United States Patent [19]

Chibata et al.

[11] 4,390,626

[45] Jun. 28, 1983

[54] IMMOBILIZED AMINOACYLASE

[75] Inventors: Ichiro Chibata, Suita; Tetsuya Tosa, Kyoto; Takao Mori, Takatsuki; Motoki Fujimura, Kyoto, all of Japan

[73] Assignee: Tanabe Seiyaku Co., Ltd., Osaka, Japan

[21] Appl. No.: 288,170

[22] Filed: Jul. 29, 1981

[30] Foreign Application Priority Data

Aug. 13, 1980 [JP] Japan .................. 55-112024

[51] Int. Cl.$^3$ .................. C12N 11/08; C12N 11/06; C12N 11/14; C12P 13/04
[52] U.S. Cl. .................. 435/176; 435/106; 435/108; 435/113; 435/180; 435/181
[58] Field of Search .............. 435/106, 108, 109, 113, 435/174, 180, 181

[56] References Cited

U.S. PATENT DOCUMENTS 3,767,531 10/1973 Olson et al. .................. 435/180
3,915,797 10/1975 Ishimatsu et al. .............. 435/106 X
4,170,696 10/1979 Hirohara et al. ............... 435/180 X
4,239,854 12/1980 Hirohara et al. ............... 435/180 X

*Primary Examiner*—David M. Naff
*Attorney, Agent, or Firm*—Jordan B. Bierman; Linda Bierman

[57] ABSTRACT

An immobilized aminoacylase is prepared by bonding aminoacylase to a water-insoluble porous anion exchanger such as a porous phenolic resin, porous styrene resin, porous silica or porous glass having anion exchange groups and treating the bonded amino-acylase with a crosslinking agent such as an aliphatic dialdehyde. The porous anion exchanger preferably has a pore size of about 150° to 3,000 A°, pore volume of about 0.3 to 1.0 m$^1$/g, specific surface area of about 10 to 150 m$^2$/g and particle size of above 0.1 to 1.2 mm. Preferred anion exchangers are trimethylammonium-introduced styrene resin and trimethylammonium-introduced silica.

10 Claims, No Drawings

IMMOBILIZED AMINOACYLASE

The present invention relates to a novel immobilized aminoacylase preparation and a method for producing thereof.

Aminoacylase is known as an enzyme which hydrolyzes an α-(N-acyl)-L-amino acid into the corresponding L-amino acid and hence the enzyme is utilized in the optical resolution of an DL-amino acid and the like.

Recently, in order to carry out an enzymatic reaction using aminoacylase continuously, the immobilization of the enzyme has been attempted. For example, there have been known the methods wherein aminoacylase is adsorbed on or conjugated with a water-insoluble support by ionic bonding, covalent bonding or gel conjugation to obtain an immobilized aminoacylase preparation. Among these methods, since the enzyme preparation can be readily obtained by a simple procedure, the immobilization of aminoacylase by ionic bonding has been often studied, though this method has disadvantages such as the enzyme is liable to leak out from a support when a concentration of a substrate to be treated or an ionic strength in a reaction system becomes high, which results in low stability of the enzyme preparation and, further, pressure drop is high when a continuous reaction is carried out by using a column packed with the enzyme preparation. For example, it has been proposed to obtain the enzyme preparation by using an anion exchange resin or a porous anion exchange resin as a water-insoluble support (Japanese Patent Publication Nos. 8835/1973 and 16954/1976).

However, these conventional techniques are still far from overcoming such disadvantage in the immobilization of aminoacylase by ionic bonding as the enzyme is liable to leak out from a support when a concentration of a substrate to be treated or an ionic strength in a reaction system is high.

As a result of the present inventors' intensive study, it has been found that an immobilized aminoacylase preparation obtained by bonding aminoacylase to a water-insoluble porous anion exchanger (hereinafter simply referred to as a porous anion exchanger) and treating the resultant with a crosslinking agent for protein has no disadvantages as described above.

One object of the present invention is to provide a novel immobilized aminoacylase preparation which has advantages such as the enzyme hardly leaks out from a support even under a high concentration of a substrate to be treated and a high ionic strength in a reaction system and, further, pressure drop during a reaction is low. Another object of the present invention is to provide a method for producing the immobilized aminoacylase preparation. These objects as well as other objects and advantages of the present invention will become apparent to those skilled in the art from the following description.

According to the present invention, there is provide an immobilized aminoacylase preparation which comprises aminoacylase and a porous anion exchanger, the aminoacylase being bonded to the porous anion exchanger and crosslinked with a crosslinking agent for protein. The immobilized aminoacylase preparation of the present invention is produced by bonding aminoacylase to a porous anion exchanger and then treating the resultant with a crosslinking agent for protein.

In the present invention, the origin of aminoacylase to be bonded to the porous anion exchanger is not critical and any aminoacylase can be used so far as it has the ability to hydrolyze an N-acyl-L-amino acid into the corresponding L-amino acid. Particularly, it is preferable to use aminoacylase having a high enzyme activity produced by fungi belonging to the genera Aspergillus, Penicillium and Mucor. Aminoacylase to be used can be obtained from its source by a known technique.

The porous anion exchanger used in the present invention is a water-insoluble porous material of an appropriate particle size having a large number of pores of about several hundreds to several thousands Å in pore size as well as large specific surface area and pore volume into which an anion exchange group has been introduced. Particularly, it is preferable to use as the porous anion exchanger a porous phenolic resin (e.g. a phenol-formaldehyde condensate), a porous styrene resin (e.g. a styrene-divinylbenzene copolymer), a porous silica or a porous glass of about 0.1 to 1.2 mm, especially 0.3 to 0.8 mm in an average particle size and having pore size of about 150 to 3,000 Å as well as specific surface area of about 10 to 150 $m^2/g$ and pore volume of about 0.3 to 1 ml/g into which a weak basic anion exchange group such as a primary, secondary or tertiary aminogroup, for example, amino, methylamino or dimethylamino; or a strong basic anion exchange group such as a quaternary ammonium group, for example, trimethylammonium or dimethylhydroxyethylammonium has been introduced. Preferred examples of the porous anion exchanger are a trimethylimmonium-introduced porous silica having pore size of about 1,000 Å, pore volume of about 0.8 ml/g, specific surface area of about 25 $m^2/g$ and particle size of 100 to 200 μm (manufactured by Rhone-Poulenc Industries under the trade name of "Spherosil QMA"); a trimethylammonium-introduced porous styrene-divinylbenzene copolymer having pore size of about 450 to 500 Å, pore volume of about 0.96 ml/g, specific surface area of about 30 $m^2/g$ and particle size of 0.35 to 0.55 mm (manufactured by Mitsubishi Chemical Industries Ltd. under the trade name of "Diaion HPA-25"); a trimethylammonium-introduced porous polystyrene having pore size of about 250 Å, pore volume of about 0.35 ml/g, specific surface area of about 25 to 35 $m^2/g$ and particle size of 0.3 to 1.2 mm (manufactured by Diamond Shamrock Corporation under the trade name of "Duolite A-161"); a dimethylhydroxyethylammonium-introduced porous polystyrene having pore size of about 250 Å, pore volume of about 0.35 ml/g, specific surface area of about 25 to 35 $m^2/g$ and particle size of about 0.3 to 1.2 mm (manufactured by Diamond Shamrock Corporation under the trade name of "Duolite A-162"); a phenolic hydroxy-introduced porous phenolic resin having pore size of about 150 Å, pore volume of about 0.7 ml/g, specific surface area of about 80 to 120 $m^2/g$ and particle size of about 0.3 to 1.2 mm (manufactured by Diamond Shamrock Corporation under the trade name of "Duolite A-561"); a trimethylammonium-introduced porous styrene-divinylbenzene copolymer having pore size of about 300 A, pore volume of about 0.5 ml/g, specific surface area of about 25 $m^2/g$ and particle size of 0.3 to 0.8 mm (manufactured by Dow Chemical Co. under the trade name of "Dowex MSA-1"); a trimethylammonium-introduced porous polystyrene having pore size of about 300 to 2,000 Å, pore volume of about 0.95 ml/g, specific surface area of about 42 $m^2/g$ and particle size of about 0.4 to 0.5 mm (manufactured by Rohm & Haas Co. under the trade name of "Amberlite IRA-904") and the like.

Examples of the crosslinking agent for protein to be used in the present invention are aliphatic dialdehydes having 2 to 6 carbon atoms such as glyoxal, malondialdehyde, succindialdehyde, glutaraldehyde, adipaldehyde and the like. Particularly, glyoxal and glutaraldehyde are preferable.

In the production of the immobilized aminoacylase preparation of the present invention, firstly, aminoacylase is bonded to the porous anion exchanger. This step is preferably carried out by contacting aminoacylase with the porous anion exchanger in water or an appropriate buffer solution. Both crude and purified aminoacylase can be used. The amount of aminoacylase to be used is depend upon the particular porous anion exchanger to be employed but, in general, it is preferable to use about 100 to 10,000 units, especially, 1,000 to 5,000 units of aminoacylase per 1 ml of the exchanger. The buffer solution includes, for example, a phosphate buffer solution and a borate buffer solution and, especially, 0.05 to 0.1 M buffer solution of pH about 7 to 9 is preferred.

The resulting porous anion exchanger to which aminoacylase has been bonded is then treated with the crosslinking agent for protein. This step is preferably carried out by contacting the exchanger with the crosslinking agent in water or a buffer solution as described above. In this step, when the concentration of the crosslinking agent is too low, crosslinking is insufficient and hence it is difficult to prevent the leakage of the enzyme from the exchanger. On the other hand, when the concentration of the crosslinking agent is too high, the enzyme is inactivated. Therefore, the amount of the crosslinking agent should be adjusted according to the amount of the enzyme adsorbed on the porous anion exchanger but, in general, it is preferable to use the crosslinking agent in a final concentration of 0.01 to 0.1% by volume based on the reaction mixture.

Alternatively, the production of the immobilized aminoacylase preparation can be also carried out by successively contacting both aminoacylase and the crosslinking agent with the porous anion exchanger in water or the above-described buffer solution. This latter reaction is more convenient than the above stepwise reaction since the desired immobilized aminoacylase preparation can be obtained in one system with more simple procedure than that in the stepwise reaction.

In both reactions, it is preferable to carry out the bonding of aminoacylase to the porous anion exchanger and the treatment with the crosslinking agent for protein at about 4° to 10° C. so as to minimize inactivation of the enzyme and to improve the adsorption and crosslinking efficiency.

The production of the immobilized aminoacylase preparation can be carried out according to either a batch process or a continuous process using a column. In case of carrying out the production according to a batch process, aminoacylase is dissolved in water or a buffer solution and added thereto the porous anion exchanger. The resulting mixture is stirred under the condition for the bonding as descibred above to form a bonded product of the exchanger and the enzyme. After the separation of the bonded product from the reaction mixture by a known technique such as decantation, filtration or centrifugation, the bonded product is added to a solution of the crosslinking agent for protein in water or a buffer solution and the mixture is stirred under the condition for the crosslinking as described above to obtain the desired immobilized aminoacylase preparation. Alternatively, when the crosslinking agent for protein is directly added to the above reaction mixture containing the bonded product and the resulting mixture is stirred under the same condition as described above, the desired immobilized aminoacylase preparation can be produced in one system. The immobilized aminoacylase preparation thus produced can be readily separated from the reaction mixture by the above known technique. In case of carrying out the production according to a continuous process using a column, water or a buffer solution containing aminoacylase is passed through a column packed with the porous anion exchanger and then water or a buffer solution containing the crosslinking agent for protein is further passed through the column to obtain the desired immobilized aminoacylase preparation. It is preferable to pass both solutions of aminoacylase and the crosslinking agent for protein through the column at SV of about 0.1 to 0.5.

When the immobilized aminoacylase preparation of the present invention is employed in an enzymatic reaction, the enzyme hardly leaks out from the porous anion exchanger even under a high concentration of a substrate to be treated and a high ionic strength in a reaction system and hence the immobilized aminoacylase preparation can maintain the stable and excellent enzyme activity for a long period of time.

The following experiments and examples further illustrate the present invention in detail but are not to be construed to limit the scope thereof.

EXPERIMENT 1

Various immobilized aminoacylase preparations were obtained as described hereinafter. Each preparation was reacted with a substrate solution continuously and the ratio of the residual enzyme activity to the initial enzyme activity was measured after a certain reaction time.

1. The production of the immobilized aminoacylase preparations
   (i) The immobilized aminoacylase preparation of the present invention Each porous anion exchanger shown in Table 1 hereinafter was swelled in water and to the swelled exchanger (10 ml) was added a solution of crude aminoacylase derived from *Aspergillus oryzae* (50 ml) [prepared by dissolving crude aminoacylase (500 mg, 15,000 $\mu$moles/h) in 0.05 M phosphate buffer (pH 7.5, 50 ml)]. To the resulting mixture was added glutaraldehyde so that the final concentration thereof in the mixture became 0.05% by volume. After shaking at 10° C. for 18 hours, the reaction mixture was filtered and the residue was washed with water to obtain the immobilized aminoacylase preparation.

(ii) The immobilized aminoacylase preparations for Control (1)

Each porous anion exchanger shown in Table 1 hereinafter was swelled in water and to the swelled exchanger (10 ml) was added a solution of crude aminoacylase derived from *Aspergillus oryzae* (50 ml) prepared by the same manner as in the above (i). After shaking at 10° C. for 18 hours, the reaction mixture was filtered and the residue was washed with water to obtain the immobilized aminoacylase preparation.

(iii) The immobilized aminoacylase preparation for Control (2)

The same procedure as described in the above (i) was repeated except that a gel-type anion exchange resin was substituted for the porous anion exchanger to obtain the immobilized aminoacylase preparation.

2. Method

Each of the above-obtained immobilized aminoacylase preparations (10 ml) was packed in a column. Aqueous 0.6 M N-acetyl-DL-methionine solution (pH 7.0, containing $5 \times 10^{-4}$ M Co$^{++}$) was passed through the column at 37° C. to carry out an enzymatic reaction. In order to measure the initial enzyme activity of the preparation, the substrate solution was passed through the column at the flow rate of 80 ml/h and the amount of L-methionine in the eluate was determined. The activity was expressed as the amount (micromoles) of L-methionine formed per 1 hour. After measuring the initial enzyme activity of the preparation, the enzymatic reaction was continued for 10 days by passing the substrate solution through the column at the flow rate of 6 ml/h. After 10 days, the residual enzyme activity of the preparation was measured according to the same procedure as in the measurement of the initial activity. The ratio of the residual activity to the initial activity was expressed in terms of the initial activity being 100.

3. Results

The results are shown in Table 1. As is clear from Table 1, the immobilized aminoacylase preparation of the present invention shows much higher residual enzyme activity than that of the control preparation and it maintains the high enzyme activty for a long period of time. To the contrary, the enzyme activity of the preparation of Control (1) is lowered with time. Besides, in the preparation of Control (1), the enzyme leakage from the support was observed even at the initial stage of the enzymatic reaction. In case of the preparation of Control (2), it was observed that the enzyme was not adsorbed on the resin at all.

TABLE 1

| Preparation | Porous anion exchanger* | Cross-linking treatment | Immobilized aminoacylase activity** Initial | After 10 days |
|---|---|---|---|---|
| Present invention | A | treated | 100 | 107 |
| | B | | 100 | 88 |
| | C | | 100 | 86 |
| | D | | 100 | 90 |
| | E | | 100 | 102 |
| | F | | 100 | 103 |
| Control (1) | A | without | 100 | 52 |
| | C | treatment | 100 | 47 |
| | F | | 100 | 37 |
| Control (2) | G | treated | 0 | — |

*The symbols A to G in Table 1 mean the following porous anion exchangers:
A: Trimethylammonium-introduced porous polystyrene having pore size of about 250 Å, pore volume of about 0.35 ml/g, specific surface area of about 25 to 35 m$^2$/g and particle size of about 0.3 to 1.2 mm (manufactured by Diamond Shamrock Corporation under the trade name of "Duolite A-161");
B: Phenolic hydroxy-introduced porous phenolic resin having pore size of about 150 Å, pore volume of about 0.7 ml/g, specific surface area of about 80 to 120 m$^2$/g and particle size of about 0.3 to 1.2 mm (manufactured by Diamond Shamrock Corporation under the trade name of "Duolite A-561");
C: Trimethylammonium-introduced porous styrene-divinylbenzene copolymer having pore size of about 300 Å, pore volume of about 0.5 ml/g, specific surface area of about 25 m$^2$/g and particle size of about 0.3 to 0.8 mm (manufactured by Dow Chemical Co. under the trade name of "Dowex MSA-1");
D: Trimethylammonium-introduced porous styrene-divinylbenzene copolymer having pore size of about 450 to 500 Å, pore volume of about 0.96 ml/g, specific surface area of about 30 m$^2$/g and particle size of about 0.35 to 0.55 mm (manufactured by Mitsubishi Chemical Industries Ltd. under the trade name of "Diaion HPA-25");
E: Trimethylammonium-introduced porous polystyrene having pore size of about 300 to 2,000 Å, pore volume of about 0.95 ml/g, specific surface area of about 42 m$^2$/g and particle size of about 0.4 to 0.5 mm (manufactured by Rohm & Haas Co. under the trade name of "Amberlite IRA-904");
F: Trimethylammonium-introduced porous silica having pore size of about 1,000 A, pore volume of about 0.8 ml/g, specific surface area of about 25 m$^2$/g and particle size of 100 to 200 μm (manufactured by Rhone-Poulenc Industries under the trade name of "Spherosil QMA"); and
G: Conventional trimethylammonium-introduced gel-type anion exchange polystyrene resin (manufactured by Diamond Shamrock Corporation under the trade name of "Duolite A-101D").

**The activity is expressed in terms of initial activity being 100.

EXPERIMENT 2

According to the same procedure as described in Experiment 1 (i) and (ii), the immobilized aminoacylase preparation of the present invention and the control preparation were obtained by using trimethylammonium-introduced porous silica having pore size of about 1,000 Å, pore volume of about 0.8 ml/g, specific surface area of about 25 m$^2$/g and particle size of about 1,000 to 2,000 μm (manufactured by Rhone-Poulenc Industries under the trade name of "Spherosil QMA").

Each immobilized aminoacylase preparation thus obtained was subjected to continuous enzymatic reactions by using N-acetyl-DL-phenylalanine (pH 7, containing $5 \times 10^{-4}$ M Co$^{++}$) and N-acetyl-DL-methionine (pH 7, containing $5 \times 10^{-4}$ M Co$^{++}$) as the substrates, respectively. The results are shown in Table 2 hereinafter.

As is clear from Table 2, the enzyme activity of the immobilized aminoacylase preparation of the present invention is stable for a long period of time. In the control preparation, since the enzyme leaked out of the reaction system even at initial stage of the reaction due to the high concentration of the substrate, the enzyme activity of the preparation was low and it was further lowered with progress of the reaction.

In view of this fact, it is apparent that the immobilized aminoacylase preparation of the present invention can exhibit superior efficiency even under a high concentration of a substrate.

TABLE 2

| Preparation | Substrate | Substrate concentration (M/l) | Immobilized aminoacylase activity* Initial | After 20 days |
|---|---|---|---|---|
| Present invention | N—acetyl-DL-methionie | 0.6 | 6,500 | 6,900 |
| | N—acetyl-DL-phenyl-alanine | 0.4 | 5,600 | 5,400 |

TABLE 2-continued

| Preparation | Substrate | Substrate concentration (M/l) | Immobilized aminoacylase activity* | |
|---|---|---|---|---|
| | | | Initial | After 20 days |
| Control | N—acetyl-DL-methionine | 0.6 | 4,300 | 1,600 |
| | N—acetyl-DL-phenylalanine | 0.4 | 3,700 | 1,400 |

*The activity is expressed in μmoles of L-amino acid formed/hour/10 ml of the immobilized aminoacylase preparation (hereinafter the same expression is used for the activity).

EXPERIMENT 3

The immobilization of aminoacylase was carried out by using the same porous anion exchanger as in Experiment 2, adding thereto a solution of crude aminoacylase derived from *Aspergillus oryzae* (50 ml) [prepared by dissolving crude aminoacylase (500 mg, 15,000 μmoles/h) in 0.05 M phosphate buffer solution (pH 7.5)], further adding thereto glutaraldehyde in the concentration shown in Table 3 and then working-up according to the same procedure as described in Experiment 1.

The resulting immobilized aminoacylase preparations, glutaraldehyde concentrations of which were different from each other were subjected to the continuous enzymatic reaction using 0.6 M/l of N-acetyl-DL-methionine as the substrate to compare their stabilities. The results were shown in Table 3.

As is clear from Table 3, when the glutaraldehyde concentration is low, the enzyme leaks out of the reaction system at an early stage of the reaction due to insufficient crosslinking. On the other hand, when the glutaraldehyde concentration is high, the enzyme activity is lowered. These result in an unfavorable lowering of the activity of the preparation.

TABLE 3

| Preparation | Concentration of glutaraldehyde (% by volume) | Immobilized aminoacylase activity | |
|---|---|---|---|
| | | Initial | After 20 days |
| Present invention | 0.005 | 5,400 | 4,300 |
| | 0.01 | 8,700 | 8,500 |
| | 0.05 | 6,500 | 6,900 |
| | 0.1 | 5,900 | 6,900 |
| Control | — | 4,300 | 1,600 |

EXAMPLE 1

Trimethylammonium-introduced porous silica having pore size of about 1,000 Å, pore volume of about 0.8 ml/g, specific surface area of about 25 m²/g and particle size of about 100 to 200 μm (manufactured by Rhone-Poulenc Industries under the trade name of "Spherosil QMA") was swelled in water. To the swelled porous silica (10 ml) was added a solution of crude aminoacylase derived from *Aspergillus oryzae* (50 ml) [prepared by dissolving crude aminoacylase (500 mg, 1,500 μmoles/h) in 0.05 M phosphate buffer solution (pH 7.5)]. Glutaraldehyde was added to the resulting mixture so that the final concentration theereof in the mixture became 0.05% by volume. After shaking at 10° C. for 18 hours, the reaction mixture was filtered and the residue was washed with water to obtain an immobilized aminoacylase preparation (10 ml).

The immobilized aminoacylase preparation (10 ml) thus obtained had the aminoacylase activity of 6,500 μmoles/h.

EXAMPLE 2

According to the same procedure as described in Example 1, an immobilized aminoacylase preparation was obtained by using trimethylammonium-introduced porous styrene-divinylbenzene copolymer having pore size of about 450 to 500 Å, pore volume of about 0.96 ml/g, specific surface area of about 30 m²/g and particle size of about 0.35 to 0.55 mm (manufactured by Mitsubishi Chemical Industries Ltd. under the trade name of "Diaion HPA-25").

The immobilized aminoacylase preparation (10 ml) thus obtained had the aminoacylase activity of 5,300 μmoles/h.

EXAMPLE 3

According to the same procedure as described in Example 1, an immobilized aminoacylase preparation was obtained by using trimethylammonium-introduced porous polystyrene having pore size of about 250 Å, pore volume of about 0.35 ml/g, specific surface area of about 25 to 35 m²/g and particle size of about 0.3 to 1.2 mm (manufactured by Diamond Shamrock Corporation under the trade name of "Duolite A-161").

The immobilized aminoacylase preparation (10 ml) thus obtained had the aminoacylase activity of 2,600 μmoles/h.

EXAMPLE 4

According to the same procedure as described in Example 1, an immobilized aminoacylase preparation was obtained by using trimethylammonium-introduced porous styrene-divinylbenzene copolymer having pore size of about 300 Å, pore volume of about 0.5 ml/g, specific surface area of about 25 m²/g and particle size of about 0.3 to 0.8 mm (manufactured by Dow Chemical Co. under the trade name of "Dowex MSA-1").

The immobilized aminoacylase preparation (10 ml) thus obtained had the aminoacylase activity of 2,200 μmoles/h.

EXAMPLE 5

According to the same procedure as described in Example 1, an immobilized aminoacylase preparation was obtained by using trimethylammonium-introduced porous styrene-divinylbenzene copolymer having pore size of about 300 to 2,000 Å, pore volume of about 0.95 ml/g, specific surface area of about 42 m²/g and particle size of about 0.4 to 0.5 mm (manufactured by Rohm & Haas Co. under the trade name of "Amberlite IRA-904").

The immobilized aminoacylase preparation (10 ml) thus obtained had the aminoacylase activity of 4,600 μmoles/h.

What is claimed is:

1. An immobilized aminoacylase preparation which consists essentially of aminoacylase and a water-insoluble porous anion exchanger selected from the group consisting of trimethylammonium-introduced styrene resin and trimethylammonium-introduced silica, wherein the water-insoluble porous anion exchanger has a pore size of about 150 to 3,000 Å, pore volume of about 0.3 to 1.0 ml/g, specific surface area of about 10 to 150 m²/g, and particle size of about 0.1 to 1.2 mm, the aminoacylase being bonded to the porous anion exchanger and crosslinked with an aliphatic dialdehyde having 2 to 6 carbon atoms.

2. A preparation according to claim 1, wherein the aliphatic dialdehyde is a member selected from the group consisting of glyoxal, malondialdehyde, succindialdehyde, glutaraldehyde and adipaldehyde.

3. A preparation according to claim 2, wherein the aliphatic dialdehyde is glyoxal or glutaraldehyde.

4. A preparation according to claim 1 wherein the porous styrene resin is trimethylammonium-introduced porous styrene-divinylbenzene copolymer.

5. A method for producing an immobilized aminoacylase preparation which consists essentially of
 (1) bonding aminoacylase to a water-insoluble porous anion exchanger selected from the group consisting of trimethylammonium-introduced styrene resin and trimethylammonium-introduced silica, wherein the water-insoluble anion exchanger has pore size of about 150 to 3,000 Å, pore volume of about 0.3 to 1.0 ml/g, specific surface area of about 10 to 150 m$^2$/g and particle size of about 0.1 to 1.2 mm, and then
 (2) treating the resultant aminoacylase bonded to the exchanger with an aliphatic dialdehyde having 2 to 6 carbon atoms to crosslink the aminoacylase.

6. A method according to claim 5, wherein the aliphatic dialdehyde is a member selected from the group consisting of glyoxal, malondialdehyde, succindialdehyde, glutaraldehyde and adipaldehyde.

7. A method according to claim 6, wherein the aliphatic dialdehyde is glyoxal or glutaraldehyde.

8. A method according to claim 5, wherein the bonding of aminoacylase to the water-insoluble porous anion exchanger was carried out by using about 100 to 10,000 units of aminoacylase per 1 ml of the exchanger.

9. A method according to claim 5 wherein the porous styrene resin is trimethylammonium-introduced porous styrene-divinylbenzene copolymer.

10. A method according to claim 5 wherein the crosslinking is carried out by using the dialdehyde in a concentration of about 0.01 to 0.1% by volume based on a reaction mixture.

* * * * *